(12) United States Patent
Ganeev et al.

(10) Patent No.: US 6,518,567 B1
(45) Date of Patent: Feb. 11, 2003

(54) METHOD FOR DETECTING ELEMENTS IN SOLUTIONS AND DEVICE FOR REALIZING THE SAME

(76) Inventors: Alexandr Akhatovich Ganeev, Home 93 Appartm. 22, Leningradskaja Street, Pushkin, 189620 St. Petersburg (RU); Sergei Evgenievich Sholupov, Home 15/30 Appartm. 28, Prospect Koroleva, 197341 St. Petersburg (RU)

( * ) Notice: Subject to any disclaimer, the term of this patent is extended or adjusted under 35 U.S.C. 154(b) by 0 days.

(21) Appl. No.: 09/646,768

(22) PCT Filed: Mar. 9, 1999

(86) PCT No.: PCT/RU99/00079
§ 371 (c)(1),
(2), (4) Date: Sep. 22, 2000

(87) PCT Pub. No.: WO99/49308
PCT Pub. Date: Sep. 30, 1999

(30) Foreign Application Priority Data

Mar. 23, 1998 (RU) .......................................... 980105314

(51) Int. Cl.[7] .......................... B01D 59/44; H01J 49/00
(52) U.S. Cl. ...................................... 250/282; 250/287
(58) Field of Search ............................... 250/282, 287, 250/423 R

(56) References Cited

U.S. PATENT DOCUMENTS

| | | | | |
|---|---|---|---|---|
| 4,344,019 A | * | 8/1982 | Gavin et al. ............ | 250/423 R |
| 5,767,512 A | * | 6/1998 | Eiden et al. ............ | 250/423 R |
| 6,011,259 A | * | 1/2000 | Whitehouse et al. ....... | 250/287 |
| 6,064,156 A | * | 5/2000 | Patterson et al. ....... | 250/423 R |

FOREIGN PATENT DOCUMENTS

| | | |
|---|---|---|
| DE | 4022061 | 1/1992 |
| GB | 2020803 | 11/1979 |
| RU | 2018818 | 8/1994 |
| SU | 226235 | 12/1968 |

OTHER PUBLICATIONS

Wei Hang, et al., "Microsecond–pulsed Glow Discharge Time–of–flight Mass Spectrometry,".

A.A. Ganeyev and S.E. Sholupov, "A thin–walled metallic hollow cathode as an atomizer for Zeeman atomic absorption spectrometry,".

* cited by examiner

*Primary Examiner*—Bruce Anderson
(74) *Attorney, Agent, or Firm*—Christopher L. Parmelee; Walker & Jocke LPA

(57) ABSTRACT

The present invention pertains to the construction of analytical instruments and may be used for analysing naturel or industrial waters, biological samples as well as geological samples. The method for detecting elements in solutions comprises pulverising the samples using pulses, ionising the pulverised atoms during Penning's collisions and recording the ions thus formed during a mass spectral analysis while carrying out a separation of the ion time-of-flight. The pulse pulverisation of the sample is carried out from a surface which is heated at a temperature of between 1000 and 1500% C. and on which the sample dried in a flow of ballast gas forms a dry residue. The ballast gas may consist of Kr, Xe or mixtures thereof wich Ar under a pressure of between 1 and 2 torrs. The device for detecting elements in solutions comprises an ionising device which is arranged in a gas-discharge chamber filled with an inert gas. The detection device further includes a time-of-flight mass spectrometer which comprises an ion sampling and focusing system as well as a reflective mass in the shape of a spectral analyser. The ionising device is made in the shape of a thin-wall, metallic, cylindrical and hollow cathode that comprises a dosing opening which is used for introducing the sample to be analysed and which is located on a same axis with a vacuum port.

7 Claims, 1 Drawing Sheet

METHOD FOR DETECTING ELEMENTS IN SOLUTIONS AND DEVICE FOR REALIZING THE SAME

BACKGROUND ART

The present invention pertains to analytical instrument manufacturing and can be used for analysing natural and industrial waters, as well as biological and geological samples.

A method is known which employs the ionic sputtering of a sample (dry solution residues) from a thin-walled metal hollow cathode in a low-pressure discharge [1]. According to this method, the cathode is heated by the discharge to a temperature of 800 to 1400° C., Kr or Xe is used as a buffer gas, and the gas pressure range lies within 10–15 Torr. Under these conditions, a so-called ionic-thermal sputtering and atomization mechanism is implemented. This mechanism enables a sample to be sputtered and atomized during a short time (0.1–1 sec), which makes it possible to attain low detection limits in various atomic absorption techniques, primarily, in the differential atomic absorption analysis. At the same time, the matrix effects are relatively weak in this method, which allows direct element determination in samples of complex composition.

A device is known for ionic-thermal sample atomization in a low-pressure discharge, which comprises an atomizer placed in a gas-discharge chamber filled with an inert gas, the atomizer being made as a cylindrical thin-walled metal hollow cathode (TWMHC) [1]. This device employs a new atomizer, which is made as a cathode heated to a temperature of 800–1400 C. by a discharge, Kr or Xe being used as the buffer gas and the gas pressure range being within 10 to 15 Torr. Under these conditions, a so-called ionic-thermal sputtering and atomization mechanism is implemented. This mechanism enables a sample to be sputtered and atomized during a short time (0.1–1 sec), which, as said above, makes it possible to attain low detection limits, the matrix effects being actually absent. Furthermore, the low power consumed by this known device (30–60 W) allows a small-size and portable analyzer to be made on its basis.

Disadvantages of the known device are its ability to detect only one element during a single analytical procedure and a comparatively high detection limit, which, for example, does not afford detecting a number of elements in natural water, environmental objects, etc. without preliminary accumulation.

A method that is most similar to the proposed invention is the one which employs pulsed gas-discharge sputtering and ionization of elements being constituents of solid conductive samples and the detection of the ions formed thereby using a time-of-flight mass spectrometer with a reflectron [2]. In Ref. [2], a standard Grimm lamp was used as a gas-discharge ionizer and the optimum pressure of the buffer gas (Ar) was 1 Torr (1.5 kPa). When using short ionizing pulses (about 10–30 Mkc), such a scheme shows high ion detection efficiency (about 20% and higher), which arises from the fact that a significant part of ions formed after a short pulsed discharge find their way into a region of action of a so-called expelling pulse, whereby the ions are injected into the mass spectrometer. As shown in [2], the relatively high ionization efficiency and stability are due to the Penning ionization of metal atoms during their collisions with metastable argon atoms.

A disadvantage of this known method is that it cannot be used to analyze solutions because of the presence of various interfering effects which appear when solutions are injected into a Grimm lamp.

A device that is most similar to the proposed invention is the one [2] in which a standard Grimm lamp is used as a gas-discharge ionizer, whereas ions formed as a result of sputtering and ionization of elements being constituents of the cathode in this lamp are detected using a time-of-flight mass spectrometer with a reflectron [2].

A disadvantage of this known device is that it cannot be used to analyze solutions because of the presence of various interfering effects which appear when solutions are injected into a Grimm lamp.

DISCLOSURE OF INVENTION

The present invention is aimed at extending the range of subjects of analysis and at lowering the detection limits.

The stated goal is achieved by the following means:

In the method for the determination of elements in solutions, which comprises the pulsed sample sputtering, the ionization of the sputtered atoms in the Penning collisions, and the detection of the ions formed thereby using the mass spectroscopic analysis with the time-of-flight ion separation, the pulsed sample sputtering is carried out from a surface heated to 1000–1500 C., whereon the sample dried in a buffer gas flow forms a dry residue, Kr or Xe, or their mixture with Ar at a pressure of 1–2 Torr being used as a buffer gas.

In the device for the determination of elements in solutions, which comprises an ionizer placed into a gas-discharge chamber filled with an inert gas and a time-of-flight mass spectrometer, which comprises an ion extraction and focusing system and a reflecting mass spectroscopic analyzer, the ionizer is made as a cylindrical thin-walled metal hollow cathode with a dispenser hole intended for injecting a sample being analyzed, which is located coaxially with a vacuum port.

Let us consider the most important points pertaining to the proposed method.

In the proposed invention, the ionic-thermal sample sputtering mechanism takes place in the ionizer, that is, in the thin-walled metal hollow cathode (TWMHC), which allows a sample to be sputtered and be partially ionized during a relatively short time (0.2–1 sec), thus making it possible to attain low detection limits in an analysis of dry residues of solutions. A relatively high, 1–2%, and, which is most important, a sufficiently stable degree of ionization is obtained due to the effective Penning ionization of atom M of a sample:

$$M+A^* \rightarrow M^+ +A, \tag{1}$$

where A and A* are, respectively, the unexcited and metastable atoms of a buffer gas.

The use of heavy Kr and Xe as a buffer gas instead of argon, which was used in [2], essentially increases the rate of sputtering [1], thereby lowering the detection limit. Furthermore, the fact that the first excitation potentials of Kr (9.9 eV) and Xe (8.7 eV) are lower than that of Ar (14 eV) results in an increase of the probability of reaction (1) (because the ionization potentials of most of the elements lie in the 6–9-eV range) and, hence, in an increase in the ion concentration and, accordingly, in the enhancement of the analyzer sensitivity. The use of Kr and Xe mixtures with Ar allows the consumption of relatively expensive gases to be reduced. At the same time, all the sputtering and Penning ionization processes will be governed by heavy noble gases, causing pertinent increase in the rates of sputtering and ionization.

At temperatures >1500 C., the high thermoelectron emission from a cathode results in expelling the field out of the cathode, which decreases the energy of the sputtering ions. In this case, the sample evaporation process appears to be of pure thermal nature, and the sample atomization and ionization time substantially increases. At temperatures <<1000 C., the rate of sputtering significantly drops. Therefore, the 1000–1400 C. temperature range is the optimum.

Note that sputtering of dry solution residues essentially differs from that of solid conductive samples. In the former case, energy E of the dry solution residue binding to the surface of a gas-discharge ionizer lies in the 1–2-eV range, whereas for solid metal samples E=5–10 eV, that is, essentially higher. As a result, the probability of sputtering of an atom being a constituent of dry solution residues is much higher than that of an atom being a constituent of a solid sample and, accordingly, the time of sputtering of a layer of same thickness is much shorter for the dry solution residues than that for the solid samples.

The optimum buffer gas pressure is governed by the following processes. At instant t after the cessation of a sputtering pulse, concentration $n^+$ of ions of an element being detected in a gas phase will be primarily governed by the ambipolar diffusion (ion loss) processes and by the Penning ionization $$dn^+/dt = -n^+/\tau_a + nA_m\exp(-(1/\tau_0 + 1/\tau_m)t), \qquad (2)$$

where n is the concentration of neutral atoms at instant t, $\tau_a$ is the time of the ambipolar diffusion of an ion to the wall of a discharge tube, $\tau_0$ is the time of the diffusion of an atom to the wall of a discharge tube, $\tau_m$ is the life time of a metastable atom of a buffer gas (allowing for the diffusion to the wall), and $A_m$ is the probability of the Penning ionization (see Eq. (1)) immediately after the cessation of the sputtering pulse. As can be seen from Eq. (2), the ion concentration $n^+$ and, accordingly, the magnitude of an ion signal will, to a significant extent, be governed by the $\tau_m$ and $\tau_0$ times, which are known to be proportional to the buffer gas pressure. Therefore, an increase in the buffer gas pressure P within a certain range will result in the ion signal increase. However, as P increases, the conditions of separation of the ions of the buffer gas and of the gases sorbed on the surface of the gas-discharge ionizer from the ions of the elements being determined will deteriorate. This separation is due to the spatial separation of the regions where the ions in the buffer gas and the atoms of the elements being detected are formed: while the ions of the buffer gas are formed in the bulk, the atoms appear near the cathode surface. For this case, the repetition rate of the sputtering pulses f should be sufficient to heat the cathode to temperatures of 1000–1500 C. To satisfy this condition, f should lie within the 500–2000-Hz range. At such repetition rates, the atoms of the elements being detected will not have enough time to diffuse on the wall of the gas-discharge chamber at pressure P>2–3 Torr (in this case, the diffusion time $\tau_0$ >300 MkC), whereby the effect of the separation of the interfering ions from those being detected will be essentially deteriorated, and this will result in a decrease in number of elements which can be detected using the proposed method and device. Hence the optimum buffer gas pressure is 1–2 Torr.

BEST MODES FOR CARRYING OUT INVENTION

Figure 1:
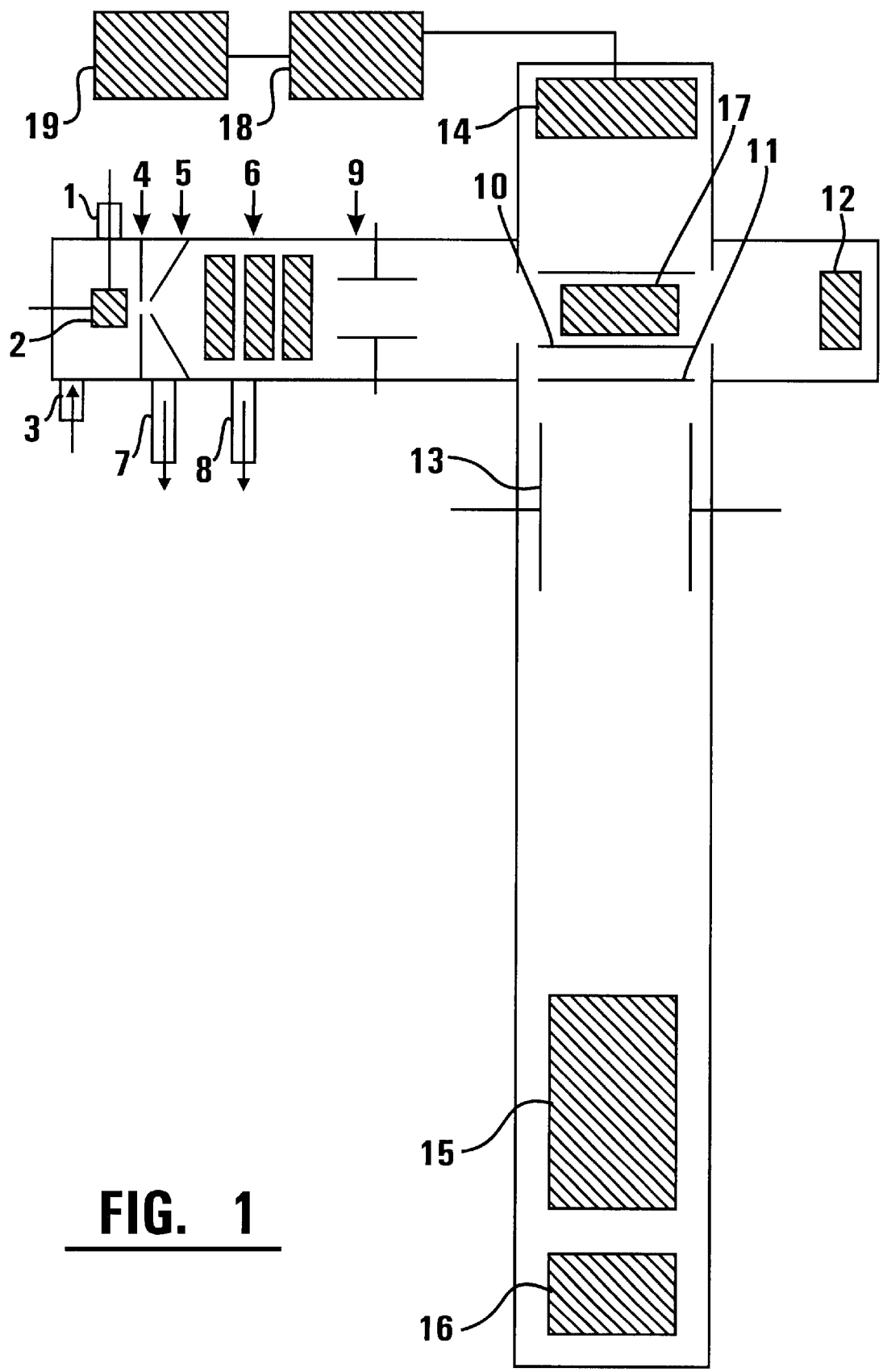
FIG. 1 shows a schematic diagram of an exemplary embodiment of a device for detecting elements in solutions.

Schematic diagram of the proposed device is shown in FIG. 1.

The device consists of automatic port 1, ionizer 2, inlet for circulation of a buffer gas 3, diaphragm 4, skimmer 5, lens system 6, ducts for differential pumping-out 7 and 8, correcting plates 9, repelling grid (10), accelerating grid 11, Faraday cell 12, correcting plates 13, microchannel plate detectors 14 and 16, reflectron 15, ion focusing region 17, high-speed analog-digital converter 18, and computer 19.

A solution sample is injected into ionizer 2 through automatic port 1. A buffer gas is pumped through port 3. Ions arrive to the mass spectrometer through diaphragm 4, skimmer 5, lens system 6, and correcting plates 9. Differential evacuation is performed through ducts 7 and 8 using backing and turbomolecular pumps. The ions that come into region 17 are injected into the mass spectrometer by a repelling pulse applied to grid 10 and are accelerated by the electric field applied to grid 11. Faraday cell 12 serves for preliminary adjustment of the system. The ions are detected by microchannel plate detectors 14 (when reflectron 15 is used) or 16 (without the reflectron) using high-speed analog-digital converter 18 and computer 19.

Thus, the claimed invention enables the range of subjects of analysis to be extended (due to incorporation of solutions) and such detection limits for solutions to be achieved that are on par or lower than those typical for any other methods of elemental analysis (without concentration).

REFERENCES

1. Ganeev A. A. and Sholupov S. E., Method of Ionic-Thermal Sample Atomization and a Device for Implementing the Same (1998).
2. Hang W., Baker C., Smith B. W., Winefordner J. D., and Harrison W. W., Microsecond-pulsed Glow Discharge Time-of-Flight Mass Spectrometry, Journal of Analytical Atomic Spectrometry, 1997, V. 12, No. 2, pp.143–150.

We claim:

1. Method for determining elements in solutions, which comprises pulsed sample sputtering, ionization of the sputtered atoms in the Penning collisions, and detecting the ions formed thereby using a mass-spectroscopic analysis with the time-of-flight ion separation, which is distinguished by the fact that the pulsed sample sputtering is carried out from a surface heated to 1000–1500 C., whereon the sample, dried in a buffer gas flow, forms a dry residue, Kr or Xe, or their mixtures with Ar at a pressure of 1–2 Torr being used as the buffer gas.

2. A method for determining elements in solutions comprising:
   a) drying a sample in a flow of a buffer gas to from a dry residue, wherein the buffer gas has a pressure in a range from 1 to 2 Torr;
   b) generating a plurality of sputtered atoms from the sample by a pulsed sample sputtering, wherein the pulsed sample sputtering is carried out from a surface heated to a temperature ranging from 1000 C. to 1500 C.;
   c) generating ions through ionization of the sputtered atoms in Penning collisions; and
   d) detecting the ions through mass-spectroscopic analysis with time-of-flight ion separation.

3. The method according to claim 2, wherein in step (a) the buffer gas includes at least one gas selected from the group consisting of Kr, Ze and Ar.

4. The method according to claim 3, wherein in step (c) the ionization is carried out with an ionizer that includes a cylindrical thin-walled metal hollow cathode with a dispenser hole for injection of the sample being analyzed.

5. The method according to claim 4, wherein in step (c) the dispenser hole is located coaxially with a vacuum port.

6. The method according to claim 5, wherein in steps (a) through (d) are carried out in a gas-discharge chamber which includes a time-of-flight mass spectrometer and an ion extracting and focusing system.

7. The method according to claim 6, wherein the time-of-flight mass spectrometer includes and a reflecting mass-spectroscopic analyzer.

* * * * *